(12) United States Patent
Luo et al.

(10) Patent No.: US 11,530,299 B2
(45) Date of Patent: Dec. 20, 2022

(54) BIOLOGICAL INK

(71) Applicant: JF POLYMERS (SUZHOU) CO., LTD., Jiangsu (CN)

(72) Inventors: Xiaofan Luo, Jiangsu (CN); Menglong Hu, Jiangsu (CN)

(73) Assignee: JF POLYMERS (SUZHOU) CO., LTD., Suzhou (CN)

( * ) Notice: Subject to any disclaimer, the term of this patent is extended or adjusted under 35 U.S.C. 154(b) by 426 days.

(21) Appl. No.: 16/475,213

(22) PCT Filed: Dec. 30, 2016

(86) PCT No.: PCT/CN2016/113391
§ 371 (c)(1),
(2) Date: Jul. 1, 2019

(87) PCT Pub. No.: WO2018/119989
PCT Pub. Date: Jul. 5, 2018

(65) Prior Publication Data
US 2019/0338079 A1    Nov. 7, 2019

(51) Int. Cl.
| | | |
|---|---|---|
| *C04B 28/14* | (2006.01) | |
| *C08K 3/32* | (2006.01) | |
| *C08F 2/46* | (2006.01) | |
| *C08F 2/50* | (2006.01) | |
| *C08G 61/04* | (2006.01) | |
| *C08G 81/02* | (2006.01) | |
| *B33Y 10/00* | (2015.01) | |
| *B33Y 70/00* | (2020.01) | |
| *B33Y 80/00* | (2015.01) | |
| *A61L 27/16* | (2006.01) | |
| *A61L 27/52* | (2006.01) | |
| *C12N 5/00* | (2006.01) | |
| *B29C 64/106* | (2017.01) | |
| *B29K 23/00* | (2006.01) | |
| *B29K 71/00* | (2006.01) | |
| *B29K 96/04* | (2006.01) | |
| *B29K 105/00* | (2006.01) | |
| *B29L 31/00* | (2006.01) | |

(52) U.S. Cl.
CPC ............ *C08G 81/025* (2013.01); *A61L 27/16* (2013.01); *A61L 27/52* (2013.01); *B33Y 10/00* (2014.12); *B33Y 70/00* (2014.12); *B33Y 80/00* (2014.12); *C12N 5/0068* (2013.01); *B29C 64/106* (2017.08); *B29K 2023/12* (2013.01); *B29K 2071/02* (2013.01); *B29K 2096/04* (2013.01); *B29K 2105/0005* (2013.01); *B29K 2105/0061* (2013.01); *B29K 2105/0085* (2013.01); *B29K 2995/0056* (2013.01); *B29L 2031/7532* (2013.01); *C12N 2533/30* (2013.01)

(58) Field of Classification Search
CPC ......... B33Y 70/00; B33Y 10/00; B33Y 80/00; C12N 5/0068; C12N 2533/30; C12M 33/00; B29L 2031/7532; A61L 27/16; A61L 27/52; C08K 5/37; C08G 63/08; C08G 81/025; B29K 2096/04; B29K 2023/12; B29K 2071/02; B29K 2105/005; B29K 2105/0085; B29K 2995/0056
USPC .......... 524/423, 418, 401, 80, 1; 522/6, 189, 522/184, 71, 1; 520/1
See application file for complete search history.

(56) References Cited

FOREIGN PATENT DOCUMENTS

| CN | 102504229 | | 6/2012 |
| CN | 103977453 | * | 8/2014 |
| CN | 104861216 | * | 8/2015 |
| CN | 105238132 | | 1/2016 |

OTHER PUBLICATIONS

Duan et al, CN 103977453 Machine Translation, Aug. 13, 2014 (Year: 2014).*
Zhou e tal, CN 104861216 Machine Translation, Aug. 26, 2015 (Year: 2015).*
International Search Report for PCT/CN2016/113391, dated Jun. 22, 2017, 4 pages.

* cited by examiner

*Primary Examiner* — Jessica Whiteley
(74) *Attorney, Agent, or Firm* — Nixon & Vanderhye P.C.

(57) ABSTRACT

The present application relates to a composition, which comprises: (a) a photopolymerizable substance; (b) a thiol; (c) a photoinitiator; (d) a thermosensitive polymer; and (e) water, and can be used as a bio-ink for preparing a bio-hydrogel for direct-writing 3D printing. The present invention further relates to a method for preparing the composition, and a direct-writing 3D printing method using the composition.

36 Claims, 1 Drawing Sheet

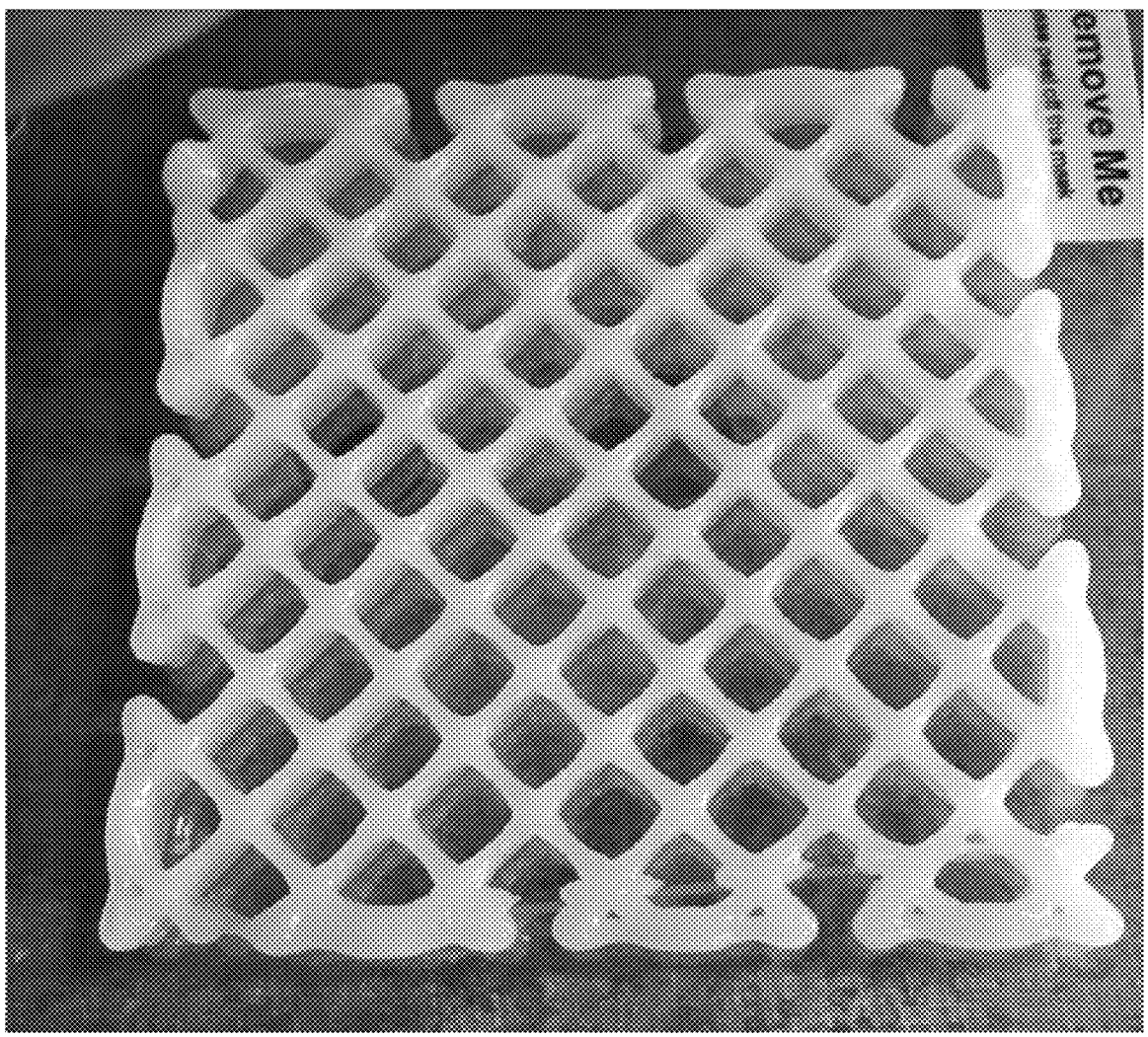

BIOLOGICAL INK

This application is the U.S. national phase of International Application No. PCT/CN2016/113391 filed 30 Dec. 2016, which designated the U.S., the entire contents of which is hereby incorporated by reference.

FIELD OF THE INVENTION

The invention relates to a composition that can be used as bio-ink for preparing bio-hydrogel for direct-writing 3D printing, a method for preparing the composition, and a direct-writing 3D printing method using the composition.

BACKGROUND ART

The ability to print hydrogel in three dimensions (3D) is crucial for the development of tissue engineering. Generally speaking, a hydrogel scaffold is made of a synthetic or natural polymer material, which provides an approach for the growth of cell tissues in vitro. One of the challenges in 3D printing of hydrogel is that most of hydrogel precursors are aqueous solutions and can't form self-supporting structures after they are extruded. Since an aqueous solution diffuses rapidly after it is extruded, the printing result doesn't have enough accuracy and resolution. Besides, the bio-ink for cell growth must have appropriate properties, such as mechanical strength, durability, and biocompatibility.

CONTENTS OF THE INVENTION

The present invention provides a bio-ink that meets the above requirements and can be used to implement a direct-writing 3D printing method.

The contents of the present invention include:

Embodiment 1

A composition, comprising:
(a) a photopolymerizable substance;
(b) a thiol;
(c) a photoinitiator;
(d) a thermosensitive polymer; and
(e) water.

Embodiment 2

The composition according to the embodiment 1, containing the photopolymerizable substance in 1 wt %-90 wt % content.

Embodiment 3

The composition according to the embodiment 1 or 2, wherein, the photopolymerizable substance is water-soluble and biocompatible.

Embodiment 4

The composition according to any of the embodiments 1-3, wherein, the photopolymerizable substance contains at least one photopolymerizable functional group.

Embodiment 5

The composition according to the embodiment 4, wherein, the photopolymerizable functional group is selected from at least one of the following groups: alkynyl, norbornyl, maleimido, fumarate, conjugated dienyl, glutarate group, or their derivatives.

Embodiment 6

The composition according to the embodiment 4, wherein, the photopolymerizable functional group is selected from at least one of the following groups:

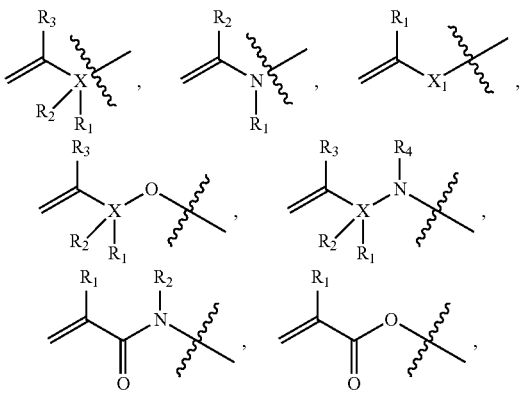

where, $R_1$, $R_2$ and $R_3$ are selected from H, halogen, alkyl, halogenated alkyl, hydroxyl, alkoxy, aryl and aryloxy groups respectively and independently wherever they appear;
X is selected from C and Si respectively and independently wherever it appears;
$X_1$ is selected from O, S, and $SO_2$ respectively and independently wherever it appears.

Embodiment 7

The composition according to any of the embodiments 1-3, wherein, the photopolymerizable substance is a monomer, an oligomer or a polymeric long-chain sub stance, wherein the monomer, oligomer or polymeric long-chain substance may be used to form the following polymers: polylactic acid, polyglycolide, polyvinyl alcohol, polyethylene glycol, polypropylene oxide, poloxamer, polyorthoester, polyanhydride, polyhydroxy acid, polydioxanone, polycarbonate, polyvinyl pyrrolidone, poly(2-ethyl-2-oxazoline), cellulose, polypeptide, polysaccharide, heparin ethylphthalate, chondroitin sulfate, alginic acid, or copolymers containing one or more of the above polymer chain segments.

Embodiment 8

The composition according to any of the embodiments 1-7, wherein, the thiol is water-soluble and biocompatible.

Embodiment 9

The composition according to any of the embodiments 1-7, wherein, the thiol comprises at least one of the following substances: sulfhydryl-containing monomers, sulfhydryl-containing oligomers, and sulfhydryl-containing macromolecular polymers.

Embodiment 10

The composition according to the embodiment 9, wherein, the thiol has at least one of the following functional groups: hydroxyl, ether, ester, carboxyl, amino, amido, or other water-soluble functional groups.

Embodiment 11

The composition according to the embodiment 9, wherein, the sulfhydryl-containing oligomers and the sulfhydryl-contain macromolecular polymers can form the following substances: polylactic acid, polyglycolide, polyvinyl alcohol, polyethylene glycol, polypropylene oxide, poloxamer, polyorthoester, polyanhydride, polyhydroxy acid, polydioxanone, polycarbonate, polyvinyl pyrrolidone, poly (2-ethyl-2-oxazoline), cellulose, polypeptide, polysaccharide, heparin ethylphthalate, chondroitin sulfate, alginic acid, or copolymers containing one or more of the above polymer chain segments.

Embodiment 12

The composition according to the embodiment 9, wherein, the thiol comprises a sulfhydryl-containing multi-branched macromolecular polymer.

Embodiment 13

The composition according to any of the preceding embodiments, wherein, the photoinitiator is water-soluble and biocompatible.

Embodiment 14

The composition according to the embodiment 13, wherein, the photoinitiator can be excited by ultraviolet light, visible light or infrared light.

Embodiment 15

The composition according to the embodiment 13, wherein, the photoinitiator comprises at least one of the following substances: free radical photoinitiators, cationic photoinitiators, or combinations thereof.

Embodiment 16

The composition according to the embodiment 15, wherein, the free radical photoinitiators comprise at least one of the following substances: methyl benzoylformate, hydroxycyclohexyl phenylketone (Irgacure 184), phenyl bis (2,4,6-trimethylbenzoyl) phosphine oxide (XBPO), mercaptobenzothiazole, Irgacure 651, Irgacure 907, Darocur 2959, camphorquinone (CQ), α-ketoglutarate (KGA), ethyl N-dimethylaminobenzoate (4EDMAB), triethanolamine (TEA), or combinations thereof.

Embodiment 17

The composition according to the embodiment 16, wherein, the cationic photoinitiators comprise at least one of the following substances: aryl diazonium salts, diaryl iodonium salts, triaryl sulfonium salts, triaryl selenium salts, triarylsulfonium hexafluoroantimonate salts, or combinations thereof.

Embodiment 18

The composition according to any of the preceding embodiments, wherein, the thermosensitive polymer has a reverse thermal gelation (RTG) property.

Embodiment 19

The composition according to any of the preceding embodiments, wherein, the thermosensitive polymer is water-soluble.

Embodiment 20

The composition according to the embodiment 18, wherein, the thermosensitive polymer is an ABA tri-block copolymer, in which block A and block B are oligomer blocks.

Embodiment 21

The composition according to the embodiment 20, wherein, the block A and block B are a hydrophobic oligomer block and a hydrophilic oligomer block respectively at a certain temperature.

Embodiment 22

The composition according to the embodiment 20, wherein, the block A and block B are a hydrophilic oligomer block and a hydrophobic oligomer block respectively at a certain temperature.

Embodiment 23

The composition according to the embodiment 22, wherein, the block A and block B contain at least one of the following blocks respectively and independently: aliphatic polyester blocks and aliphatic polyether blocks.

Embodiment 24

The composition according to the embodiment 22, wherein, the block A is a polyethylene oxide block and the block B is a polypropylene oxide block.

Embodiment 25

The composition according to the embodiment 22, wherein, the thermosensitive polymer is a multi-block copolymer having a structural formula (ABA-X)m, in which A and B are oligomers respectively and independently wherever they appear, m is an integer within a range of 1-30, and X is a chain extender.

Embodiment 26

The composition according to the embodiment 25, wherein, the chain extender X is binary, ternary or polyisocyanate, binary, ternary or polycarbonate or acyl halide, or a combination thereof respectively and independently wherever it appears.

Embodiment 27

The composition according to the embodiment 25, wherein, the block A and block B are a hydrophilic oligomer block and a hydrophobic oligomer block respectively at a certain temperature.

Embodiment 28

The composition according to the embodiment 25, wherein, the block A and block B are a hydrophobic oligomer block and a hydrophilic oligomer block respectively at a certain temperature.

Embodiment 29

The composition according to the embodiment 25, wherein, the ABA multi-block macromolecular polymer comprises at least one of the following substances: polyurethane, polycarbonate, polyester, or combinations thereof.

Embodiment 30

The composition according to any of the preceding embodiments, wherein, the thermosensitive polymer comprises poly(N-substituted acrylamide).

Embodiment 31

The composition according to the embodiment 30, wherein, the poly(N-substituted acrylamide) is poly(N-isopropyl acrylamide) (NIPAM).

Embodiment 32

The composition according to the embodiment 20, wherein, the thermosensitive polymer comprises at least one of the following substances: derivatives of polyvinyl alcohol, hydroxypropyl methyl cellulose (HPMC), hydroxyethyl ethyl cellulose (EHEC), or combinations thereof.

Embodiment 33

The composition according to any of the preceding embodiments, wherein, the composition is used to prepare a bio-hydrogel for direct-writing 3D printing.

Embodiment 34

A method for preparing the composition according to any of the preceding embodiments, comprising: mixing the components of the composition to a homogenous state.

Embodiment 35

A method for printing a bio-hydrogel in direct-writing 3D printing, comprising the following steps:
extruding the composition according to any of the embodiments 1-34 to form a linear material; irradiating the linear material with light so that the linear material has a photopolymerization reaction; laying the linear material on a substrate to form a hydrogel scaffold. Accordingly, the present invention further relates to a method for preparing a hydrogel scaffold, which comprises: extruding the composition according to any of the embodiments 1-34 to form a linear material; irradiating the linear material with light so that the linear material has a photopolymerization reaction; laying the linear material on a substrate to form a hydrogel scaffold.

Embodiment 36

The method according to the embodiment 35, wherein, the step of irradiating the linear material with light so that the linear material has a photopolymerization reaction is executed at one or more of the following moments:
(a) Simultaneously with the step of extruding the bio-ink through a micro-nozzle;
(b) After the extruded linear material is laid on the substrate; and
(c) After the hydrogel scaffold is fully formed.

The ink has outstanding 3D printing performance and excellent cell biocompatibility.

BRIEF DESCRIPTION OF DRAWINGS

FIG. 1 shows a hydrogel scaffold obtained from the composition provided in the present invention with the direct-writing 3D printing method provided in the present invention.

DETAILED DESCRIPTION OF THE EMBODIMENTS

The present invention provides a hydrogel precursor aqueous solution (i.e. bio-ink) and a hydrogel produced through cross-linking of the solution. The hydrogel can be printed by 3D printing to produce a cell growth scaffold. Besides, the present invention provides a method for preparing the bio-ink and printing a cell growth scaffold by 3D printing.

Direct writing is a 3D printing technique for printing hydrogel scaffolds. Using that technique, materials can be assembled layer by layer to create layered or predetermined 3D hydrogel structures, shapes, and micro-periodicity.

A hydrogel scaffold may be formed by one or more layers of interconnected rod-shaped structures stacked together. The width (or diameter) of those rod-shaped structures ranges from 10 μm to 500 μm, and the clearance between them ranges from 5 μm to 500 μm. Generally speaking, a scaffold formed by direct writing consists of 1-20 layers. Such scaffolds may be arranged periodically in one dimension, two dimensions, or three dimensions.

Hydrogel scaffolds are widely applied in tissue engineering. Hydrogel scaffolds can provide outstanding cell activity, and have certain mechanical strength to facilitate transplantation. The porous structure of the hydrogel scaffold facilitates cell integration and tissue growth, and prompts the formation of new blood vessels in the tissue. An advantage of using direct-writing 3D printing to construct a hydrogel scaffold lies in: with this technique, the porosity, pore size and interconnection among the pores in the scaffold can be controlled and adjusted very conveniently.

A typical direct-writing 3D printer generally includes a three-axis positioning platform and a syringe fixed on the positioning platform for storing bio-ink. When the positioning platform moves to a predetermined position, the ink is extruded through the nozzle to form a linear material, and the linear material is laid on a substrate (e.g., glass substrate). After printing a first layer, the printing head gradually moves upward in the Z-axis direction, and thereby starts to print a second layer. That process is repeated continuously, till the desired 3D structure is fully printed. The step of driving the extruded linear material to have a photopolymerization reaction by light curing may be executed at one of the following moments:
(a) simultaneously with the step of extruding the bio-ink through a micro-nozzle; (b) after the extruded linear material is laid on the substrate; (c) after the hydrogel scaffold is fully formed.

The extruded hydrogel line consists of two phases: an uncured phase and a cured phase, which are different from each other in elasticity.

The uncured phase of the hydrogel line consists of a pure physically entangled polymer network, and that physical gel structure has elasticity viscosity behaviors suitable for extrusion through a nozzle. In contrast, the cured phase of the hydrogel line consists of a physically cross-linked polymer network and a chemically cross-linked polymer network. For example, such bio-ink may contain a long-chain macromolecular polymer and a photopolymerizable monomer, which can form an interpenetrating physical and chemical gel structure after light curing. This interpenetrating physical and chemical gel structure has better mechanical strength than the pure physically entangled polymer network.

In another scenario, the cured phase may contain a chemically cross-linked polymer network, but doesn't contain physically entangled polymer chains. Such bio-ink may include physically entangled polymer chains that are chemically modified. Photopolymerizable functional groups are introduced into the two ends or main chains of such polymer chains. After the light curing, the long-chain polymer can crosslink itself, and thereby the physical gel structure changes into a chemical gel structure.

The key to direct-writing 3D printing is the material used in the direct-writing 3D printing, i.e. a precursor solution or "ink". It is required that the ink can be extruded through the nozzle into a linear shape, and can cure quickly to maintain the printed shape. Eligible bio-ink may contain a long-chain polymer and a photopolymerizable substance (e.g., a monomer, an oligomer or a polymer that contains at least one photopolymerizable functional group). The ink may further contain a crosslinker, a photoinitiator, and water.

Polymers may have linear structures or multi-branched structures. The molecular chain of a linear polymer is a simple long chain. If short molecular chains that have the same repetitive units as the main chain appear at irregular frequencies on the long chain of the polymer, the polymer is referred to as a branched polymer; if short molecular chains that have repetitive units different from the repetitive units of the main chain appear at irregular frequencies on the long chain of the polymer, the polymer is referred to as a grafted copolymer; if each repetitive unit of the long chain of the polymer contains the same short molecular chain, the polymer is referred to as a comb-like polymer. If the polymer contains branched chains radiating outward centering on a small molecule, the polymer is referred to as a star-like polymer. Compared with linear polymers that only contain one or two functional groups, multi-branched polymers can contain more functional groups.

Chain extenders are also known as chain growing agents, and they are substances that can react with the functional groups on linear polymer chains to extend the molecular chains and increase the molecular weight. They are often used to improve the mechanical and processing properties of polymers.

By adjusting the molecular weight of the long-chain polymer, the type of the photopolymerizable substance, the number of functional groups, or the molecular structure (linear or multi-branched structure) of the photopolymerizable substance, and the concentration of the photopolymer and the crosslinker, the properties of the ink and the hydrogel can be adjusted to achieve specific printing parameters, so as to adapt to different printing systems.

Biological cells may be directly mixed into the bio-ink. In such a case, what is printed out by the direct-writing 3D printing is a 3D hydrogel structure that encapsulates the cells. Alternatively, the biological cells may be attached to the hydrogel surface after the hydrogel scaffold is printed.

Since the bio-ink will be used in biological applications, it must have outstanding biocompatibility. According to the definition in ISO10993, biocompatibility refers to the performance of the tissues of an organism that react to a non-vital material. It usually refers to the compatibility between the material and the host, including tissue compatibility and blood compatibility. ISO10993 includes 17 relevant standards, including Guidelines for Biological Evaluation of Medical Devices and Biomaterials (ISO10993-1).

The Bio-3D printed hydrogel will be contact with living cells and transplanted into a human body after the cells grow. Therefore, according to the requirements in ISO10993, bio-ink for Bio-3D printing must meet the following standard biological evaluation methods: 10993-3—Genotoxicity, Carcinogenicity and Reproductive Toxicity Test, 10993-4—Selection of Blood Interaction Test, 10993-5—Cytotoxicity Test (in Vitro), 10993-6—Local Reaction Test after Implantation, 10993-10—Stimulation and Sensitization Test, and 10993-11—Systemic Toxicity Test.

The bio-ink may contain a photopolymerizable substance. That substance may be a monomer, an oligomer or a macromolecular polymer that contains at least one photopolymerizable functional group, such as hydroxyethyl methacrylate or polyethylene glycol diacrylate. In the process of photopolymerization, the photopolymerizable substance forms a chemically cross-linked polymer network, and forms an interpenetrating structure with the long-chain polymer in the bio-ink. The concentration of the photopolymerizable substance in the bio-ink may be 5 wt %-55 wt %.

Usually, the UV wavelength for polymer photopolymerization ranges from 250 nm to 420 nm, and the intensity of light irradiation is 50 mW/cm$^2$ to 2 W/cm$^2$. The exposure intensity of the hydrogel scaffold under UV light depends on the intensity and duration of the UV light irradiation. If the exposure intensity is not high enough, photopolymerizable substance may be unable to crosslink fully, and consequently the mechanical strength of the hydrogel scaffold can't reach an ideal level. However, if the exposure intensity is too high, the cells in the bio-ink may be injured by the UV light.

An oxygen inhibition effect in free radical polymerization is the biggest obstacle to direct-writing 3D printing. Oxygen quenches the increase of photoinitiator production, and consequently hinders free radical polymerization. In direct-writing 3D printing, the diameter of the extruded bio-ink lines is only several hundreds of microns, and the oxygen inhibition effect is more prominent here, because the lines have a larger area of contact with oxygen. Under the action of the oxygen inhibition effect, the surface of the hydrogel may not cure fully, or even can't cure. Therefore, the oxygen inhibition effect is a major obstacle to direct-writing 3D printing on the scale of several hundreds of microns. Possible ways to avoid the influence of the oxygen inhibition effect on the curing of the material include: printing under nitrogen shielding; irradiating with UV light at very high intensity; or increasing the concentration of the photoinitiator. However, cells can't survive in a nitrogen atmosphere for a long time. High-intensity UV exposure and high-concentration photoinitiators may be harmful to cell activity.

The invention utilizes a thiol-ene reaction to avoid the obstacle of oxygen inhibition effect to direct-writing 3D printing. Oxygen molecules react with free carbon radicals or free thiol radicals to produce peroxide radicals. Peroxide radicals do not quench the polymer chain extending reaction, but take away the hydrogen atoms on thiol and thereby form another free thiol radical, so that the polymer chain extending reaction can continue. In that way, the oxygen inhibition effect is avoided.

The water-soluble long-chain polymer in the bio-ink must be maintained at adequate concentration so that the polymeric molecules can physically entangle with each other in the bio-ink. Thus, the bio-ink will have a shear thinning property. Usually, the concentration of the water-soluble long-chain polymer is between 1% and 90%. The specific value depends on the physical properties and molecular weight of the water-soluble polymer.

In order to successfully print a porous 3D structure by direct-writing 3D printing, the extruded structure must be self-supporting: the extruded material can remain in a linear shape and don't require any additional supporting structure. A self-supporting structure can avoid structural deformation in the printing process.

In order to be self-supporting, the bio-ink must have a significant shear thinning property, which is to say, the shear storage modulus (G') of the bio-ink must be much greater than the shearing loss modulus (G"). In that way, the bio-ink remains in a stable state when the applied stress is lower than a threshold; when the applied stress is equal to or greater than the threshold in direct-writing 3D printing, the bio-ink can flow.

When pressure is applied to the syringe filled with bio-ink, the shearing stress at the nozzle is equal to or greater than the shearing stress threshold, thus the bio-ink shear-thinned at the nozzle. The shearing loss modulus (G") must be low enough so that the bio-ink can be easily extruded from the nozzle. Once the bio-ink is extruded from the nozzle, the shearing stress is lower than the shearing stress threshold. The shearing storage modulus (G') must be high enough so that the extruded bio-ink lines can support themselves and maintain the shape after extrusion. In that way, the extruded hydrogel scaffold can maintain its 3D structure. That process may be carried out in a sterile buffer environment, so that the cells remain active while they are extruded with the bio-ink through the printer nozzle.

In the preparation of the bio-ink, it is very important to uniformly disperse different components to form a homogeneous liquid, because an inhomogeneous mixture may cause the nozzle clogged, result in light curing failure, or have adverse effects to the growth of the cells. However, it is very difficult to mix bio-ink with a shear thinning property to a homogeneous state in the traditional way. Thermosensitive polymers with a reversed thermal gelation property present a solution. These polymers have a low critical transition temperature (LCST) after they are dissolved in water:

The water solution is a low-viscosity liquid at low temperatures, and therefore it is easy to mix with other components to form a homogeneous liquid.

When the temperature is higher than the gel temperature ($T_{gel}$), the viscosity of the water solution increases; thus a physically entangled network of the thermosensitive polymer is formed and a hydrogel is produced. At its gel point, the bio-ink has an excellent shear thinning property, which is beneficial for extrusion through the nozzle.

Compared with reverse thermal gelation polymers, the water solution of a traditional thermal gelation polymer is a low-viscosity liquid at high temperatures.

If the water solution of a traditional thermal gel polymer is used to prepare the bio-ink, the mixing has to be carried out at a high temperature. The high temperature will have adverse effects to the cells adulterated in the bio-ink. Alternatively, the extrusion through the nozzle has to be performed at a low temperature, which is difficult to achieve technically.

The viscosity of high-concentration water solution of polyethylene glycol-polypropylene glycol-polyethylene glycol (PEO-PPO-PEO) copolymer changes significantly between 4-40° C. and exhibits a reversed thermal gelation property. The results of researches indicate that the significant viscosity change occurs because the micelle concentration tends to be a critical volume fraction 0.53, which leads to "hard-sphere crystallization".

In addition to the micelle system of PEO-PPO-PEO copolymer, another reverse thermal gelation polymer is hydroxyethyl ethyl cellulose (EHEC). The water solution of hydroxyethyl ethyl cellulose and the corresponding ionic surfactants gel at a high temperature, and then liquefy again when the temperature drops to be below the gel point. The main reason for the gelation is the complexation between the surfactant and the hydroxyethyl ethyl cellulose polymer at a high temperature. As the temperature increases, the agglomeration of the surfactant declines, while the ionization degree of the agglomerates increases. The hydrophobic part of hydroxyethyl ethyl cellulose complexes with those agglomerates, resulting in cross-linking and gelation.

Another reverse thermal gelation polymer is poly(N-isopropyl acrylamide). The water solution of poly(N-isopropyl acrylamide) undergoes volumetric phase transition at about 33.6° C., and changes from a swelling gel to a shrinking gel. That change is resulted from the hydrophobicity of the poly(N-isopropyl acrylamide) polymer. Polymers tend to agglomerate by means of intermolecular hydrogen bonding, resulting in phase separation. The arrangement of poly(N-isopropyl acrylamide) is more orderly in a weak solution than in a concentrated solution, because relatively strong hydrogen bonds can be formed between the polymer and water molecules. As the temperature increases, the strength of those hydrogen bonds will decrease; consequently, the previous structure will become unstable, and gelation will happen.

EMBODIMENTS

Embodiment 1

In ice bath, 20 g polyethylene glycol diacrylate (molecular weight~200) is dissolved in 80 g deionized water. Then, 25 g Pluronic F127 (polyoxyethylene-polyoxypropylene ether block copolymer), 2 g dithiothreotol, and 3 g α-ketoglutarate are added into the polyethylene glycol diacrylate solution. The mixture is stirred in ice bath to obtain a homogenous solution. The solution is poured into a syringe. When the temperature of the solution returns to room temperature, the syringe can be installed on a direct-writing 3D printer. A mesh-formed 3D model file is run in the printer, and the positioning platform moves along a path set by the program; at the same time, the bio-ink is compressed by a pneumatic piston and extruded on the surface of a glass substrate. While the bio-ink is extruded into a linear material, the UV light source (365 nm wavelength, 150 mW/cm$^2$) equipped on the printer is turned on for light curing. After the printing is completed, a mesh-formed hydrogel scaffold is obtained (FIG. 1). The obtained hydrogel scaffold is soft and elastic, and can be used for cell culturing after it is sterilized.

Embodiment 2

In ice bath, 20 g polyethylene glycol diacrylate (molecular weight~200) is dissolved in 80 g deionized water. Then, 25 g Pluronic F127 (polyoxyethylene-polyoxypropylene ether block copolymer), 1.5 g dithiothreotol, and 5 g hydroxycyclohexyl phenylketone (Irgacure 184) are added into the polyethylene glycol diacrylate solution. The mixture is stirred in ice bath to obtain a homogenous solution. The solution is poured into a syringe. When the temperature of the solution returns to room temperature, the syringe can be installed on a direct-writing 3D printer. A mesh-formed 3D model file is run in the printer, and the positioning platform moves along a path set by the program; at the same time, the bio-ink is compressed by a pneumatic piston and extruded on the surface of a glass substrate. While the bio-ink is extruded into a linear material, the UV light source (365 nm wavelength, 150 mW/cm$^2$) equipped on the printer is turned on for light curing. After the printing is completed, the obtained hydrogel scaffold is further exposed under the UV light source equipped on the printer for 2 minutes to make the hydrogel scaffold cure further. The obtained hydrogel scaffold is soft and elastic, and can be used for cell culturing after it is sterilized.

Embodiment 3

In ice bath, 20 g polyethylene glycol diacrylate (molecular weight~200) is dissolved in 80 g deionized water. Then, 25 g Pluronic F127 (polyoxyethylene-polyoxypropylene ether block copolymer), 2.5 g dithiothreotol and 3.6 g methyl benzoylformate are added into the polyethylene glycol diacrylate solution. The mixture is stirred in ice bath to obtain a homogenous solution. The solution is poured into a syringe. When the temperature of the solution returns to room temperature, the syringe can be installed on a direct-writing 3D printer. A mesh-formed 3D model file is run in the printer, and the positioning platform moves along a path set by the program; at the same time, the bio-ink is compressed by a pneumatic piston and extruded on the surface of a glass substrate. The UV light source equipped on the printer is not turned on when the bio-ink is extruded into a linear material. Instead, after the printing is completed, the obtained hydrogel scaffold is exposed under the UV light source (365 nm wavelength, 150 mW/cm$^2$) equipped on the printer for 5 minutes to make the hydrogel scaffold cure. The obtained hydrogel scaffold is soft and elastic, and can be used for cell culturing after it is sterilized.

The invention claimed is:

1. A composition, comprising:
   (a) a photopolymerizable substance;
   (b) a thiol;
   (c) a photoinitiator;
   (d) a thermosensitive polymer; and
   (e) water
   wherein the photopolymerizable substance is a monomer, an oligomer, or a polymeric long-chain substance, and wherein the monomer, oligomer or polymeric long-chain substance may be used to form one or more of the following polymers: polylactic acid, polyglycolide, polyvinyl alcohol, polyethylene glycol, polypropylene oxide, poloxamer, polyorthoester, polyanhydride, polyhydroxy acid, polydioxanone, polycarbonate, polyvinyl pyrrolidone, poly(2-ethyl-2-oxazoline), cellulose, polypeptide, heparin ethylphthalate, chondroitin sulfate, alginic acid, or copolymers containing one or more of the above polymer chain segments,
   wherein the composition is homogeneous and
   wherein the photopolymerizable substance, thiol, photoinitiator, and thermosensitive polymer are biocompatible.

2. The composition according to claim 1, containing the photopolymerizable substance in 1 wt %-90 wt % content.

3. The composition according to claim 1, wherein, the photopolymerizable substance comprises at least one photopolymerizable functional group selected from alkynyl, norbornyl, maleimido, fumarate, conjugated dienyl, glutarate group, and their derivatives.

4. The composition according to claim 3, wherein, the photopolymerizable functional group is selected from the following groups:

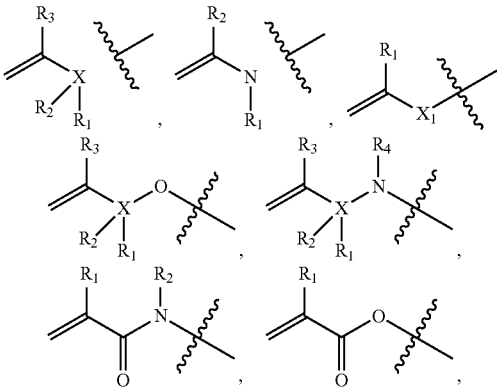

where, $R_1$, $R_2$ and $R_3$ are selected from H, halogen, alkyl, halogenated alkyl, hydroxyl, alkoxy, aryl and aryloxy groups respectively and independently wherever they appear;

X is selected from C and Si respectively and independently wherever it appears;

$X_1$ is selected from O, S, and $SO_2$ respectively and independently wherever it appears.

5. The composition according to claim 1, wherein, the photopolymerizable substance is polyethylene glycol diacrylate.

6. The composition according to claim 1, wherein, the thiol is dithiothreotol.

7. The composition according to claim 1, wherein, the thiol comprises at least one of the following substances: sulfhydryl-containing monomers, sulfhydryl-containing oligomers, and sulfhydryl-containing macromolecular polymers.

8. The composition according to claim 7, wherein, the thiol has at least one functional group selected from the following functional groups: hydroxyl, ether, ester, carboxyl, amino, amido, or other water-soluble functional groups.

9. The composition according to claim 7, wherein, the sulfhydryl-containing oligomers and the sulfhydryl-contain macromolecular polymers can form the following substances: polylactic acid, polyglycolide, polyvinyl alcohol, polyethylene glycol, polypropylene oxide, poloxamer, polyorthoester, polyanhydride, polyhydroxy acid, polydioxanone, polycarbonate, polyvinyl pyrrolidone, poly(2- ethyl-2-oxazoline), cellulose, polypeptide, polysaccharide, heparin ethylphthalate, chondroitin sulfate, alginic acid, or copolymers containing one or more of the above polymer chain segments.

10. The composition according to claim 7, wherein, the thiol comprises a sulfhydryl-containing multi-branched macromolecular polymer.

11. The composition according to claim 1, wherein, the photoinitiator can be excited by ultraviolet light, visible light or infrared light.

12. The composition according to claim 1, wherein, the photoinitiator comprises at least one of the following substances: free radical photoinitiators, cationic photoinitiators, or combinations thereof.

13. The composition according to claim 12, wherein, the free radical photoinitiators comprise at least one of the following substances: methyl benzoylformate, hydroxycyclohexyl phenylketone (Irgacure 184), phenyl bis(2,4,6-trimethylbenzoyl) phosphine oxide (XBPO), mercaptobenzothiazole, 1,2-diphenyl-2,2-dimethoxyethanone, 2-methyl-4'-(methylthio)-2-morpholinopropiophenone, 2-hydroxy-4'-(2-hydroxyethoxy)-2-methylpropiophenone,
camphorquinone (CQ), α-ketoglutarate (KGA), ethyl N-dimethylaminobenzoate (4EDMAB), triethanolamine (TEA), or combinations thereof.

14. The composition according to claim 12, wherein, the cationic photoinitiators comprise at least one of the following substances: aryl diazonium salts, diaryl iodonium salts, triaryl sulfonium salts, triaryl selenium salts, triarylsulfonium hexafluoroantimonate salts, or combinations thereof.

15. The composition according to claim 1, wherein, the thermosensitive polymer has a reverse thermal gelation property.

16. The composition according to claim 15, wherein, the thermosensitive polymer is an ABA tri-block copolymer, in which block A and block B are oligomer blocks.

17. The composition according to claim 16, wherein, the block A and block B are a hydrophobic oligomer block and a hydrophilic oligomer block respectively at a certain temperature.

18. The composition according to claim 16, wherein, the block A and block B are a hydrophilic oligomer block and a hydrophobic oligomer block respectively at a certain temperature.

19. The composition according to claim 18, wherein, the block A and block B contain at least one of the following blocks respectively and independently: aliphatic polyester blocks and aliphatic polyether blocks.

20. The composition according to claim 18, wherein, the block A is a polyethylene oxide block and the block B is a polypropylene oxide block.

21. The composition according to claim 18, wherein, the thermosensitive polymer is a multi-block copolymer having a structural formula (ABA-X)m, in which A and B are oligomers respectively and independently wherever they appear, m is an integer within a range of 1-30, and X is a chain extender.

22. The composition according to claim 21, wherein, the chain extender X is binary, ternary or polyisocyanate, binary, ternary or polycarbonate or acyl halide, or a combination thereof respectively and independently wherever it appears.

23. The composition according to claim 21, wherein, the block A and block B are a hydrophilic oligomer block and a hydrophobic oligomer block respectively at a certain temperature.

24. The composition according to claim 21, wherein, the block A and block B are a hydrophobic oligomer block and a hydrophilic oligomer block respectively at a certain temperature.

25. The composition according to claim 21, wherein, the ABA multi-block macromolecular polymer comprises at least one of the following substances: polyurethane, polycarbonate, polyester, or combinations thereof.

26. The composition according to claim 1, wherein, the thermosensitive polymer comprises poly(N-substituted acrylamide).

27. The composition according to claim 26, wherein, the poly(N-substituted acrylamide) is poly(N-isopropyl acrylamide) (NIPAM).

28. The composition according to claim 16, wherein, the thermosensitive polymer comprises at least one of the following substances: derivatives of polyvinyl alcohol, hydroxypropyl methyl cellulose (HPMC), hydroxyethyl ethyl cellulose (EHEC), or combinations thereof.

29. The composition according to claim 1, wherein, the composition is formulated for preparing a bio-hydrogel for direct-writing 3D printing.

30. A method for preparing the composition according to claim 1, comprising:
mixing the components of the composition to a homogenous state.

31. A method for printing a bio-hydrogel in direct-writing 3D printing, comprising the following steps:
extruding the composition according to claim 1 to form a linear material; irradiating the linear material with light so that the linear material has a photopolymerization reaction;
laying the linear material on a substrate to form a hydrogel scaffold.

32. The method according to claim 31, wherein, the step of irradiating the linear material with light so that the linear material has a photopolymerization reaction is executed at one or more of the following moments:
(a) simultaneously with the step of extruding the bio-ink through a micro-nozzle;
(b) after the extruded linear material is laid on the substrate; and
(c) after the hydrogel scaffold is fully formed.

33. The composition according to claim 1, wherein the photopolymerizable substance is polyethylene glycol diacrylate, the thiol is dithiothreotol, and the thermosensitive polymer is polyoxyethylene-polyoxypropylene ether block copolymer.

34. The composition according to claim 1, wherein the photopolymerizable substance is polyethylene glycol diacrylate, the thiol is dithiothreotol, the thermosensitive polymer is polyoxyethylene-polyoxypropylene ether block copolymer, and the photoinitiator is α-ketoglutarate, hydroxycyclohexyl phenylketone, or methyl benzoylformate.

35. A composition obtained from photopolymerization of the composition of claim 1 under UV light with a wavelength of 250 nm to 420 nm and an intensity of 50 mW/cm$^2$ to 2 W/cm$^2$.

36. A composition obtained from photopolymerization of the composition of claim 34 under UV light with a wavelength of 250 nm to 420 nm and an intensity of 50 mW/cm$^2$ to 2 W/cm$^2$.

* * * * *